US010898466B2

(12) United States Patent
Muran

(10) Patent No.: US 10,898,466 B2
(45) Date of Patent: *Jan. 26, 2021

(54) METHODS AND COMPOSITIONS FOR REDUCING OR ELIMINATING SYMPTOMS OF WITHDRAWAL FROM DRUGS AND ALCOHOL

(71) Applicant: Longevity Healthcare Center, Newport Beach, CA (US)

(72) Inventor: Peter J. Muran, Newport Beach, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/530,602

(22) Filed: Aug. 2, 2019

(65) Prior Publication Data

US 2020/0069641 A1 Mar. 5, 2020

Related U.S. Application Data

(63) Continuation of application No. 16/117,648, filed on Aug. 30, 2018, now Pat. No. 10,485,783.

(51) Int. Cl.
*A61K 31/375* (2006.01)
*A61K 9/00* (2006.01)
*A61K 31/167* (2006.01)
*A61P 25/32* (2006.01)
*A61P 25/36* (2006.01)
*A61K 9/08* (2006.01)

(52) U.S. Cl.
CPC .......... *A61K 31/375* (2013.01); *A61K 9/0019* (2013.01); *A61K 9/08* (2013.01); *A61K 31/167* (2013.01); *A61P 25/32* (2018.01); *A61P 25/36* (2018.01)

(58) Field of Classification Search
CPC .. A61K 31/375; A61K 9/0019; A61K 31/167; A61K 25/32; A61K 25/36; A61K 9/08
See application file for complete search history.

(56) References Cited

U.S. PATENT DOCUMENTS

| 4,432,975 | A | 2/1984 | Libby |
| 4,500,515 | A | 2/1985 | Libby |
| 8,044,096 | B2 | 10/2011 | Lines |

FOREIGN PATENT DOCUMENTS

WO 2017212113 A1 12/2017

OTHER PUBLICATIONS

Long et al. www.ennDoc's.net Emergency Medicine EducationAlcohol Withdrawal: Pearls and Pitfalls Jun. 28, 2016 (16 pages).*
Stone, Irwin, The Natural History of Ascorbic Acid in the Evolution of the Mammals and Primates and Its Significance for the Present-Day Man, pp. 82-89.
Root-Bernstein et al. "A Common Molecular Motif Characterizes Extracellular Allosteric Enhancers of GPCR Aminergic Receptors and Suggests Enhancer Mechanism of Action". Cirrent Medicinal Chemistry, 2014, pp. 3673-3686.
Wu, PhD., Defeng et al. "Alcohol, Oxidative Stress, and Free Radical Damage". http://pubs.niaa.nih.goc/publications/arh27-4/277-284.htm.
Zeraati, Fatemeh et al. "Ascorbic Acid Interaction With Angelsic Effect of Morphine and Tramadol in Mice" https://www.ncbi.nlm.nih.gov/pmc/articles/PMC4183085/.
Evangelou, A et al. "Ascorbic Acid (vitamin C) effects on Withdrawal syndrome of heroin abusers." https://www.ncbi.nlm.nih.gov/pubmed/10836211.
Libby, Alfred F. et al. "A Study Indicating a Connection Between Paranoia, Schizophrenia, Perceptual Disorders, and I.Q. in Alcohol and Drug Abusers" Orthomolecular Psychiatry, vol. 11, No. 1, 1982, pp. 50-66.
Schauss, PhD, Facn Alexander G. "Attenuation of Heroin Withdrawal Syndrome by the Administration of High-Dose Vitamin C", JOM vol. 27, No. 4, 2012, pp. 189-197.
Milivojevic, Verrica et al. "Central and Peripheral Biomarkers of Stress Response for Addiction Risk and Relapse Vulnerability", Trends in Molecular Medicine, Feb. 2018, vol. 24, No. 2, pp. 173-186.
Pauling, Linus "Evolution and the Need for Ascorbic Acid", Proceddings of the National Academy of Sciences, vol. 67, No. 4, Dec. 16, 1970. pp. 1643-1648.
Warner, Timothy A. et al. "Low brain ascorbic acid increases susceptibility to seizures in mouse models of decreased brain ascorbic acid transport and Alzheimer's disease" Epilepsy Res. Feb. 2015. Author Manuscript pp. 1-10.
De La Torre, Rafael et al. "MDMA, mehtamphetamine and CYP2D6 pharmacogenetics: what is clinically relevant?", Frontiers in Genetics, Nov. 2012, vol. 3, Article 235, pp. 1-8.
Libby, Alfred F. et al. "Methodology: Use of Orthomolecular Techniques for Alcohol and Drug Abuse, in a Post-Detox Setting" Orthomolecular Psychiatry, vol. 11, No. 4, 1982. pp. 277-288.
Cecil, Cam et al. "DNA methylation and substance-use risk; a prospective, genome-wide study spanning gestation to adolescence" Transl Psychiatry (2016) pp. 1-9.
Skrabalova, Jitka et al. "Morphine as a Potential Oxidative Stress-Causing Agent" https://www.ncbi.nlm.nih.gov/pmc/articles/PMC3871421.
Pinto-Covarrubias, Adriana et al. "Old Things New View: Ascorbic Acid Protects the Brain in Neurodegenerative Disorders" International Journal of Molecular Sciences. 2015. pp. 28194-28217.

*Primary Examiner* — Shirley V Gembeh
(74) *Attorney, Agent, or Firm* — Carlos A. Fisher; Stout, Uxa & Buyan, LLP

(57) ABSTRACT

Methods and compositions of reducing or eliminating the symptoms of withdrawal from drug or alcohol in drug or alcohol-dependent persons, while restoring the patient to nutritional health. The methods including parenteral administration of solutions containing high doses of ascorbic acid; while the compositions of the invention comprise at least about 20% (w), or at least about 25% (w), or at least about 30% (w), or at least about 35% (w), or at least about 38% (w) of ascorbic acid and a local anesthetic.

17 Claims, No Drawings

(56) References Cited

OTHER PUBLICATIONS

Putchala MC et al. "Ascorbic acid and its pro-oxidant activity as a therapy for tumours of oral cavity—a systematic review." Arch Oral Biol. 2013.

Penberthy, W. Todd et al. "Supplements Accelerate Benzodiazepine Withdrawal: A Case Report and Biochemical Rationale." Orthomolecular Medicine News Service , Mar. 18, 2014.

Wayner, D.D.M. et al. "The antioxidant efficiency of vitamin C is concentration-dependent" https://www.sciencedirect.com/science/article/pii/0304416586902345?via%3Dihub.

Libby, Alfred F. et al. "The Hyperascorbemia-Kwashiorkor Approach to Drug Addiction Therapy: A Pilot Study" https://www.seanet.com/~alexs/ascorbate/197x/libby-af-orthomol_psych-1977-v6-n4-p300.htm.

Libby, Alfred F. et al. "The Junk Food Connection" a Study Reveals Alcohol Adversely Affect Metabolism and Behavior.

Surtees, Robert et al. "Treatable neonatal epilepsy" www.orchidschild.com.

Myrick M.D., Hugh et al. "Treatment of Alcohol Withdrawal" Alcohol Health & Research World vol. 22 No. 1. 1998. pp. 38-43.

Baker, Dale, "Vitamin C and Glutathione" https://g6pdeficiency.org/wp/2013/04/15/vitamin-c-and-glutathione/#/WtUb62aZOum.

Libby Institute. Date Unknown.

Klimant et al. Current Oncology Apr. 2018; 25(2): 139-148.

Carr and McCall J Transl Med (2017) 15:77; 1-14.

Free et al. Orthomolecular Psychiatry, 7(4) 1978; 264-270.

Nauman et al. Antioxidants 2018, 7,89:1-22.

Gao et al. Mediators of Inflammation, 207, Article ID 402467, 12 pages.

\* cited by examiner

METHODS AND COMPOSITIONS FOR REDUCING OR ELIMINATING SYMPTOMS OF WITHDRAWAL FROM DRUGS AND ALCOHOL

FIELD OF THE INVENTION

This invention is drawn to compositions and methods pertaining to a treatment for reducing or eliminating the physical symptoms of withdrawal from substances of abuse (SOA), such as habit-forming drugs and alcohol. The described methods and compositions are capable of reducing or totally and rapidly detoxifying the subject while inhibiting or reducing manifestation of withdrawal symptoms and eliminating the intense physiological/psychological craving for the SOA. At the same time, the present methods and compositions restore and rebuild the nutritional health of the patient.

BACKGROUND OF THE INVENTION

Drug addiction and alcoholism are serious personal, social and economic problems. Particularly in view of the current opioid epidemic, addictive opioid drugs such as heroin, morphine, oxycontin, methadone, buprenorphine, fentanyl, etc., as well as addictive non-opioid drugs including cocaine, barbiturates, benzodiazepines, methamphetamine, are abused in the United States at record rates. Addition to SOAs exacts a terrible price in suffering, overdoses, and a high financial cost, to society as a whole.

Among all SOAs, alcohol addiction is the number one killer, being responsible for 88,000 deaths per year in the United States. according to the National Institutes of Health; all other drugs (illicit and prescription) combined resulted in 64,000 overdose deaths per year in the U.S. in 2017.

Vast sums of money are spent in treatment and rehabilitation programs in an effort to treat drug addition and alcoholism and return the addict to health. As illicit drugs tend to be expensive, it is not uncommon for an addict to engage in criminal enterprises, such as robbery or theft, to obtain the money necessary to support his or her drug habits. According to the National Institute of Alcohol Abuse and Alcoholism the estimated annual cost of alcohol abuse alone in the U.S. as of 2010 was $249 billion dollars. When the costs of drug abuse (including tobacco and prescription drug misuse) are included, the total annual economic cost of drug and alcohol abuse increased to more than $750 billion dollars per year.

Current approaches to heroin and other opioid addiction include "maintenance" programs using opioid heroin analogs such as methadone and buprenorphine as a substitute for the illicit narcotic, such as heroin. Under such maintenance programs, the patient continues to be addicted to the analog (which is usually less potent as an intoxicant than the SOA) until or unless the patient wishes to taper off the analog. These analog compounds may be combined with the opioid receptor antagonist naloxone (sold under the trade name Narcan®) to prevent misuse of the "substitute". Thus, these maintenance methods are self-defeating because methadone and buprenorphine, while less intoxicating on a molar basis than heroin, are themselves addicting. Such maintenance methods therefore merely substitute an illegal form of drug addiction for another, legal form; the patient remains addicted to drugs. Moreover, the analogs themselves may be abused or combined with other drugs, resulting in overdose and death. In 2004 methadone contributed to 3,849 deaths in 2004; in most cases in combination with other drugs, especially benzodiazapines.

Another approach to opioid addiction is "cold turkey" withdrawal, where the addict refrains from ingesting the SOA. This may be done voluntarily, but is more often that the patient is either physically restrained from using the drug, or placed within a drug rehabilitation facility as a condition of probation or parole. Withdrawal from opiates is characterized by severe muscle spasms, chills, lacrimation, depression, anxiety, digestive problems, diarrhea, fatigue, vomiting, and a continuing physical craving for the narcotic. The "cold turkey" method involves a not inconsiderable amount of pain and for this reason is dreaded and avoided by addicts.

Withdrawal from opiates alone does not usually involve seizures or a risk of death. However, withdrawal from certain other drugs (such as benzodiazepines, barbiturates and alcohol) can result in grand mal seizures and an increased risk of death without medical intervention.

A further method of drug detoxification has been the use of drugs such as sedatives (e.g., Valium (diaxepam) and other benzodiazepines)), and analgesics (such as Darvon (propoxyphene, an opioid now banned by the FDA due to serious side effects) to attempt to reduce the patient's withdrawal symptoms from the offending drug.

Alcohol withdrawal may range in severity from mild tremors to convulsions, delirium tremens (DTs) and death. Such symptoms typically begin to occur between 6 and 48 hours after heavy alcohol consumption decreases.

Various methods are used to wean an alcoholic from dependency on alcohol. Current approaches to alcoholism may include the administration of doses of alcohol to the patient ("alcohol loading") to induce sickness, after which unpleasant confrontations are initiated to stimulate aversion to drinking.

There is also the electrode method of stimulus-response to create aversion. An alcoholic is given a drink and as the drink is raised to the lips he or she receives an uncomfortable electric stimulus in order to create an aversion to drinking.

In chemical variations of this method, the initially detoxed patient is given a daily dose of an acetaldehyde dehydrogenase inhibitor such as disulfiram (sold under the trade name "Antabuse®"). After ingesting disulfiram when even small amounts of alcohol are consumed the patient may experience "hangover" symptoms such as flushing, throbbing in head and neck, throbbing headache, respiratory difficulty, nausea, copious vomiting, sweating, thirst, chest pain, palpitation, dyspnea, hyperventilation, tachycardia, hypotension, syncope, marked uneasiness, weakness, vertigo, blurred vision, and confusion. Severe reactions caused, for example, by ingestion of large amounts of alcohol may result in death.

Cold turkey detoxification from alcohol is discouraged at least in cases of moderate to severe alcohol withdrawal due to the risk of serious adverse reactions or death.

All the above approaches, and others known to date, treat alcoholism or drug addiction as a problem to be treated essentially by preventing access to, and ingestion of, the offending substance. All these methods require anywhere from 72 hours to 21 days, with accompanying withdrawal symptoms, to accomplish detoxification, which is a slow and painful process. While sedatives can ease anxiety, none of these methods significantly reduce either withdrawal symptoms or the continuing craving for the addictive substance.

Although electrolyte balance is currently addressed in the treatment of alcohol withdrawal, only slight attention, if any, is directed toward a patient's overall nutritional health or lack thereof when withdrawing from addictive substances.

Libby, A. & Stone, I., THE HYPOASCORBEMIA-KWASHIORKOR APPROACH TO DRUG ADDICTION THEPAPY: A PILOT STUDY, (Lecture Presented at the Western Regional Seminar of the International Academy of Preventive Medicine, San Francisco, Calif. (Jul. 16, 1977) presents theory and study data concerning the use of Vitamin C and the 20 essential amino acids in the treatment of addiction.

Libby, U.S. Pat. No. 4,500,515, describes a method and composition for detoxifying from addicts and alcoholics using about 10 g to about 15 g sodium ascorbate. The method comprises administering high oral doses of sodium ascorbate until the patient experiences diarrhea, and then switching to parenteral administration of the remainder of a critical total blocking dose of 28 to 35 grams of sodium ascorbate in a first day of treatment.

Lines, U.S. Pat. No. 8,044,096, discloses a method for treating addition using a combination of Vitamin C, Vitamin $B_3$ and quercetin in specific weight ratios.

All patents, patent publications and non-patent publications cited herein are hereby individually incorporated herein by reference in their entirety. No admission is hereby made that any such reference is prior art to the present invention.

There is therefore need for a method for rapidly detoxifying drug and/or alcohol addicts that also effectively blocks withdrawal symptoms, reduces or eliminates the physical craving effect, and quickly returns the patient to a greater level of nutritional health, with a minimum of interruption in employment and other activities of daily life.

SUMMARY OF THE INVENTION

The present patent application is drawn to methods and compositions for the treatment of drug and/or alcohol dependency, including addiction to opioids such as heroin, morphine, oxycontin, methadone, buprenorphine, fentanyl, etc., as well as addictive non-opioid drugs including cocaine, barbiturates, benzodiazepines, methamphetamine, nicotine and alcohol dependency, which addresses the symptoms of substance abuse and withdrawal as a metabolic problem. In its most complete aspects, the method addresses detoxification, elimination of withdrawal symptoms, and rehabilitation.

Although not intending to be limited by theory, Applicant believes that chronic drug and alcohol dependencies result in, and may be exacerbated by, a general and severe lack of nutritional health, such that patient show signs similar to those seen in people suffering from Kwashiorkor (severe protein-calorie malnutrition) and scurvy (Vitamin C deficiency). The applicant has also found that withdrawal symptoms from SOAs, including severe cravings, can be reduced or eliminated by quickly restoring nutritional health to the patient by the use of methods involving the sequential parenteral administration of two or more applications containing different concentrations of ascorbic acid, with other vitamins, minerals, amino acids, and electrolytes.

In addition to providing nutrients, the present methods also involve the use of compositions, such as compositions containing nutrients, vitamins, anti-oxidants and/or methylation-promoting agents, that nourish the alcoholic's and addict's usually malnourished body and remove toxic oxidized compounds and free radicals from the body, or target such compounds and free radicals for excretion by the body. These processes of restoring nutritional health and eliminating metabolic waste from the body.

Although not intending to be limited by theory, Application believes that drugs and alcohol enter and leave to body in four stages:

1) absorption by the body depends on how the drug is administered. Drugs administered orally—by eating, drinking, or swallowing pills—are absorbed through the stomach and small intestine. Oral administration is by far the predominant mode of alcohol use. The drug then passes through the liver before entering the bloodstream. Substances administered this way take effect more slowly than drugs taken via other routes, such as smoking or injection.

Injection is one of the fastest ways for SOAs to reach body tissues and organs through the bloodstream. Injection into the vein—or intravenous injection—delivers the substance directly into the bloodstream. Injection into the muscle allows the substance to be absorbed into the bloodstream through the muscle tissue, and this is called an intramuscular injection. A subcutaneous injection is an injection into the fatty tissue underneath the skin, which enables the substance to be absorbed through the fatty tissue into the bloodstream. An intradermal injection is an injection into the skin tissue.

Transdermal administration of illicit drugs is not as common as oral administration or injection. Substances that are administered this way are applied to the skin and then absorbed into the body. Once the drug is absorbed through the skin, it enters the bloodstream to be carried throughout the body and possibly to the brain.

Some drugs can be inhaled as gases. Gases penetrate the lining of the lungs very quickly, which allows the drug to enter the bloodstream.

Nasal inhalation of crushed drugs causes them to be absorbed through the blood vessels in the nose where they enter the blood stream. This is similar to how buccal and sublingual drugs are absorbed. Buccal drugs are placed between a person's gums and cheek, and sublingual drugs are placed under a person's tongue. Buccal and sublingual drugs dissolve in the mouth and are absorbed through the tissue in the mouth to enter the bloodstream.

2) Distribution occurs via the body's circulatory system. Once an SOA has entered the bloodstream, the heart pumps the blood throughout the body, eventually carrying the substance to the brain.

Before a drug can enter the central nervous system it must pass through the blood-brain barrier, a system of tightly woven capillaries, that act as a barrier to prevent blood-borne pathogens and poisons from reaching the brain. Some drugs that are intended to act on the central nervous system are specially designed to pass through this barrier; other drugs simply appear to have the ability to pass through the blood-brain barrier innately.

Once the SOA has reached the brain, it can have various effects, including inducing euphoria or the "high" that is commonly associated with SOA use. SOAs accomplish this by affecting the neurotransmitters and neuroreceptors within the brain. Alcohol and many drugs affect dopamine levels, which results in feelings of pleasure and reward.

The act of distribution is also responsible for the many negative side effects that drugs can have on the body. Because substances are carried to the entire body through the blood, they can have many unintended effects on the heart, liver, stomach, lungs, and/or other internal organs.

3) Metabolism: Once a drug has been distributed throughout the body, it is broken down or metabolized. The amount of time a drug stays in the body before being broken down varies between substances and methods of administration. All substances that enter the bloodstream, regardless of how they are administered, are eventually carried to the liver to be metabolized. Although the liver is the primary site of drug metabolism, drug metabolism may also occur in various other tissues and organs, such as the kidneys, lungs, skin, and other sites.

The liver metabolizes SOAs through its enzymes, which break down the drugs, while attempting to obtain energy from the metabolic process. In so doing, the SOA is transformed into substances that can be easily expelled by the body, typically through the breath, urine or feces. Some drugs, however, produce metabolites that have deleterious effects on the body. Most SOAs (e.g. alcohol, amphetamines, opiates and benzodiazepines) promote the generation of reactive oxygen species such as free radicals. Reactive oxygen species (ROS) are small, highly reactive, oxygen-containing molecules that are naturally generated in small amounts during the body's metabolic reactions and can react with and damage complex cellular molecules such as fats, proteins, or DNA, thereby interfering with the body's normal defense mechanisms against these compounds through numerous processes. Alcohol produces deleterious ROS effects particularly in liver tissue, while opioids and amphetamines produce deleterious ROS effects in the brain and in intracellular organelles such as the mitochondria. The metabolism of benzodiazepines also produce ROS effects in the brain and in intracellular organelles such as the mitochondria and in DNA.

4) Finally, the last phase of a SOA within the body is excretion. This is the process by which the SOA exits the body, primarily via urine or feces. The metabolized drug travels from the liver to the bladder and large intestine, where waste products carry what is left of the drug out of the body. Additionally, some waste products are transported to the lungs and excreted as a gas.

The reaction of ROS with antioxidants, or through the restoration of vitamins and minerals that help the body remove or inactivate ROS constitutes an important part of portion of the detoxification of the present invention.

The detoxification methods, systems, and compositions of the present invention provide for the substantial removal of intoxicants from the body of a human suffering from alcohol dependency or drugs of abuse within about 4-7 hours after commencing the parenteral administration of the compositions, and with little or none of the common symptoms of drug or alcohol withdrawal. This is true without regard to whether the patient is drug or alcohol-free when the parenteral treatment is commenced, or not. Continued treatment in accordance with the methods and compositions of the invention continues to restore the body to health and to reduce or eliminate the physical and/or psychological symptoms of withdrawal.

Ascorbic Acid

The compositions of the present invention comprise a treatment regimen comprising the use of high doses of Vitamin C, along with high doses of B vitamins, minerals, methylation agents, anti-oxidants and certain amino acids at prescribed rates of administration. Preferably, the method involves the parenteral application of aqueous compositions containing at least two different concentrations of ascorbic acid (or an water soluble ascorbate salt), at least one of said compositions comprising a antioxidative dose of ascorbic acid at a concentration in said composition close to, but less than, saturation.

Without wishing to be limited by theory, it is believed that ascorbic acid can inhibit the analgesic activity of morphine by binding to opioid receptors, such as the opioid μ receptor.

Ketamine and ascorbic acid share anti-depressive activity and this appears to be modulated through the $GABA_A$ and $GABA_B$ receptors. The anti-depressive activity of both agents act synergistically with a $GABA_A$ receptor agonist, and are blocked by a $GABA_B$ receptor agonist. Rosa, et al., Pharmacological Reports Vol 68, Issue 5 996-1001 (October 2016

When rats are permitted to self-administer morphine for 2 hours per day on 10 consecutive days, then injected intraperitoneally with ascorbic acid, the level of self-administration (i.e. the number of lever pressings) and number an intensity of withdrawal symptoms decrease. See Alaei et al., Pathophysiology, Vol. 12, No. 2, 103-107 (September 2005).

In studies of morphine-induced withdrawal syndrome after morphine cessation, is has been found that nitric oxide synthase (NOS) and phospholipase A2 may increase free radicals, and that inhibitors of these enzymes and free radical scavengers (e.g. anti-oxidants such as Vitamin C) may attenuate withdrawal symptoms. See e.g., Mori, T., Behav. Pharmacol. 18(8) 725-9 (December 2007). Interestingly, Ascorbic acid also acts as a pro-oxidant at high concentrations under physiological conditions. Ascorbic acid's pro-oxidation activity arises as part of a dose-dependent bimodal activity, from its routine antioxidant property to generate free radicals at concentrations from 3-5 mM in vitro and 0.5-about 2 mM ex vivo in humans.

The liver enzyme L-gulonolactone oxidase is the final enzyme in a pathway of enzymes utilized by the mammalian liver to synthesize ascorbic acid from glucose. This biosynthesis of ascorbic acid is a conserved, vital and basic synthetic pathway occurring in nearly all living organisms, both plant and animal.

However, in the course of evolution a primate ancestor of man suffered a conditional lethal mutation on the site of the gene controlling the production of the enzyme L-gulonolactone oxidase, destroying its ability to produce an active enzyme, and thus all its progeny from being able to synthesize ascorbic acid. Among mammals only man, certain monkeys, guinea pigs, and an Indian fruit eating bat (*Pteropus medius*) are unable to produce ascorbic acid in their livers. These few species are the only mammals that can contract and die of scurvy if deprived of exogenous ascorbic acid.

Hippocrates was the first to document that scurvy is a disease. Since the 15$^{th}$ century it has been known that citrus fruit would cure scurvy; however, this knowledge has been lost and regained continually through history. For example, during the Age of Exploration (between 1500 and 1800), it has been estimated that scurvy killed at least two million sailors.

The Nobel Prize-winning biochemist Linus Pauling, extrapolating from the rate of Vitamin C synthesis in rats of about 26-58 mg/day×kg, and assuming proportionality to both species and body weight, estimated that the optimal rate of intake of Vitamin C in man would be about 2 g to about 3 g per day under normal circumstances if the L-gulonolactone oxidase gene was not inactivated by mutation. When a person is under stress (e.g., when infected by a common cold virus), this optimum amount may increase significantly.

Ascorbic acid is concentrated in the brain, which is responsible for 25% of total glucose utilization. Such high activity correlates with a high oxidative metabolism requiring high levels of antioxidants for protection against pathological conditions. Under normal brain activity ascorbic acid, sequestered in glial reservoirs, is released to the synaptic cleft, wherein it is taken up by neurons to scavenge reactive oxygen species (ROS) generated during synaptic activity and neuronal metabolism. In this process ascorbic acid is oxidized to dehydroascorbic acid, and released into the extracellular space, where it can be recycled by astrocytes.

When orally administered, the amount of ascorbic acid that can be administered is limited by its laxative activity within the GI tract. Oral doses of up to about 2-5 g of Vitamin C at one time will normally cause diarrhea. The FDA recommended daily dose for an adult is 40 mg per day.

Previous attempts at Vitamin C-mediated detoxification methods emphasize the necessity for the oral administration of relatively large doses of ascorbic acid, such as about 4 to 8 grams of ascorbic acid every 2 hours, for a total of six hours or until the patient experiences diarrhea. See e.g., Libby, U.S. Pat. No. 4,500,515, col 2, lines 55-60. These prior methods indicate that diarrhea must be stimulated because it is "believe[d] to be absolutely necessary in order to decontaminate the body, as well as [to] reinitiate normal peristalsis of the bowel." Libby et al., ORTHOMOLECULAR PSYCHIATRY, Vol. 11, No. 4, 277 (1982) at 282 (emphasis in original).

By contrast, in the present application the applicant finds that not only is the initiation of diarrhea not necessary for decontamination of the body, but in preferred embodiments diarrhea is most vehemently to be avoided as part of the detoxification process. This is not only because diarrhea causes the patient to become dehydrated, but also because diarrhea may exacerbate serious gastrointestinal disorders such as irritable bowel syndrome (IBS) or Crohn's disease from which some patients may already suffer.

Furthermore, patients suffering from chronic alcohol dependency often suffer from cirrhosis of the liver; both excessive alcohol consumption and cirrhosis are risk factors in the development of bleeding esophageal varices, which can quickly become a fatal esophageal hemorrhage. Stimulation of substantial peristaltic movement in the GI tract by the oral ingestion of ascorbic acid in amounts that result in what has been described as "explosive" diarrhea may risk a hemorrhage or bleeding of bowel or esophageal tissue.

In one example, the method of the invention comprises parenterally infusing into a patient a detoxifying composition comprising at least 10 g of ascorbic acid, or a salt thereof. As used herein, ascorbic acid may comprise L-ascorbic acid, R-ascorbic acid and/or racemic ascorbic acid. Ascorbate salts are readily water-soluble ascorbate salts and may comprise, for example, potassium ascorbate and/or sodium ascorbate. Unless specifically indicated otherwise, the term "ascorbic acid" shall mean one or more of ascorbic acid and an ascorbate salt.

The detoxifying composition may comprise 10 g or more of ascorbic acid or ascorbate salt in solution at a concentration of greater than 0.2 grams/ml, and administered at an average rate of at least about 0.5 ml/minute. Preferably, the detoxifying composition may comprise at least about 25 g ascorbic acid or an ascorbate salt in solution. Preferably, the detoxifying composition may have a concentration of ascorbic acid or ascorbate salt of about 0.5 g/ml or more. In presently preferred examples, the detoxifying composition is parenterally administered at an average rate of at least about 1.0 ml/min.

Preferably, the detoxifying composition comprises a local anesthetic. The detoxifying composition may be administered parenterally by hand "push" (e.g., using a syringe) so as to modulate the instantaneous rate at which the composition is administered, such that the instantaneous rate of administration may be momentarily reduced or increased according to the patient's comfort level and vital signs.

Preliminary Patient Encounter

Preferably, about 2-4 days prior to performing the methods, and administering the compositions, of the present invention, information is first gathered, and the patient is then started on a preparatory oral regimen, as follows:

A first patient encounter typically includes,
a) obtaining an extensive medical history and physical examination from the patient; and
b) ordering laboratory tests based on genetic, blood and urine analysis:

These tests may include:

1) A test for glucose-6-phosphate dehydrogenase (G6PD) enzyme deficiency. The results of this test are essentially a "go/no go" indicator for the suitability of a patient for the methods described herein.

If a patient is G6PD deficient, their red blood cells lyse easily, leading to hemolytic anemia, and such patients should not be given doses of ascorbic acid greater than about 500 mg.

2) obtaining genomic testing for single nucleotide polymorphisms (SNP) in the subject's DNA. SNPs are defined as a variation in a single nucleotide that occurs at a specific position in the genome (generally within the coding sequence of a gene), where each variation is present to some appreciable degree within a population. SNPs can be determinants for disease states; diseases such as sickle cell anemia, β-thalassmia and cystic fibrosis result from SNPs.

SNPs can occur in genes involved in methylation pathways; a well-known SNP is in the methylene tetrahydrofolate reductase (MTHFR) gene which normally breaks down homocystienese variants. Catalogs and databases of vatrious SNP are well known and widely available. For example, academic, governmental, and private databases exist which list SNPs (see the National Institutes of Health web page https://www.ncbi.nlm.nih.gov/snp). Additionally, DNA sequence testing laboratories are widely accessible now, from private testing sites such as from www.23andme.co. Companies like 23andMe, Inc. also possess SNP databases that can be accessed and used to determine whether a given person's genome contains any particular identified SNP, and matches such a person's genome to known genetic alleles contained in the SNP database.

3) blood concentration of the amino acid homocystiene. High levels are associated with a greater than average risk of heart attack, stroke or blood clots, and levels should be lowered before beginning drug detoxification therapy.

4) drugs of abuse serum and urine screen.

5) CMP (Complete metabolic panel): This test includes blood tests for:

glucose, which is the major energy source for the body; a steady supply must be available for use, and a relatively constant level of glucose must be maintained in the blood.

calcium; essential for the proper functioning of muscles, nerves, and the heart and is required in blood clotting and in the formation of bones.

serum albumin; produced in the liver and serves as a carrier for agents such as water, cations such as $Ca^{++}$, $Na^+$ and $K^+$, fatty acids, hormones, bilirubin, thyroxine (T4) and drugs (including barbituates). Low serum albumen may be caused by liver disease, nephrotic syndrome, burns, loss of protein from the gastrointestinal system, malnutrition, late pregnancy, genetic variations and malignancy. High serum albumin indicates dehydration.

total serum protein.

electrolytes (e.g., sodium, potassium, $CO_2$, chloride).

(BUN (blood urea nitrogen) urea; (a nitrogenous compound) is normally filtered out of the blood by healthy kidneys; high serum urea is an indicator of kidney malfunction.

Creatine; a waste product produced in the muscles; it is normally filtered out of the blood by the kidneys so blood levels are a good indication of how well the kidneys are working.

Liver tests: ALP (alkaline phosphatase)—enzyme found in the liver and other tissues, bone; elevated levels of ALP in the blood are most commonly caused by liver disease or bone disorders; ALT (alanine amino transferase, also called SGPT)—enzyme found mostly in the cells of the liver and kidney; a useful test for detecting liver damage; AST (aspartate amino transferase, also called SGOT)—enzyme found especially in cells in the heart and liver; also a useful test for detecting liver damage.

6) CBC (complete blood count)

7) Hepatitis virus panel for hepatitis A virus, hepatitis B virus, and hepatitis C virus).

Go/No Go Decision Point

Based on certain of the results obtained from the blood, urine and DNA testing (for example, without limitation, a finding of G6PD deficiency; a positive HIV test result; or an active hepatitis infection) a decision may be made that a particular patient is not suitable for the detoxification method if the present invention, either permanently (such as in the case of G6PD deficiency) or temporarily (such as in the case of an active hepatitis A infection).

Customizing the Compositions to the Patient

Assuming that the test results fail to indicate that the patient is presently unsuitable for treatment. In other cases, such as in the identification and screening of short polynucleotide polymorphisms (SNPs) associated with the methylation or demethylation of compounds or regulatory nucleic acids. Methylation of gene promoter regions is often associated with the suppression of gene transcription in these genes, while demethylation of such regulatory regions may be associated with "up-regulation" of transcription from this gene. In some cases, the SNP data can provide information permitting the clinician to increase or decrease the dosage and identities of methylation and methyltransferase agents (such as S-adenosyl methionine, or SAM-e) and vitamins and minerals that which can aid in promoting liver function and be helpful in the treatment of depression, atherosclerosis, and osteoarthritis.

Preferably, the patient is seen 3-4 days prior to the first day of treatment. It is at this time that the personal history is taken, the physical examination is performed, and the laboratory tests are ordered. Also at this time patient is familiarized with the detoxification method and program, and given an idea of what to expect during treatment.

After having obtained test results and determined that the patient is suitable for the detoxification treatment and does not have glucose-6-phosphate dehydrogenase deficiency, the patient is begun on a daily oral regimen of vitamin and mineral supplements, preferably at least 2-3 days prior to parenteral detoxification.

The oral regimen will typically involve two daily supplement packets: a morning (AM) dose and an evening (PM) dose.

In one embodiment, a first supplement packet may comprise: about 1 gram of ascorbic acid; about 250 mg of B complex vitamins (at least vitamins B1, B2, B3, B5, B6, B7, B9 and B12); about 400 mg of S-adenosyl methionine (SAM-e); about 400 mg of methyl tetrahydrofolate (MTHF); about 600 mg N-acetyl cysteine (NAC); and about 500 mg tyrosine.

In one embodiment, a second supplement packet may comprise: about 1 gram of ascorbic acid; about 500 mg of glutamine; about 500 mg of GABA (gamma-aminobutyric acid or 4-aminobutanoic acid); about 1 gram of tryptophan; about 100 mg of 5-hydroxy tryptophan; about 5000 units of Vitamin D; about 0.5 mg melatonin; about 2 μg selenium; and about 25 mg zinc.

Some recent research finds GABA accumulation in the synaptic cleft of the amygdala to be associated with an inability to internalize GABA by some post synaptic neurons. See Rainer Spanagel, Aberrant Choice Behavior in Alcoholism, Science 360:6395 1298-1299 (Jun. 22, 2018). Thus, in some embodiments of the present invention addition of GABA is avoided in any oral of parenteral composition.

In other embodiments a single daily oral supplement packet may contain any or all of the ingredients of the first supplement packet and/or the second supplement packet described above.

In another embodiment the first supplement packet is given as a morning (AM) dose.

In another embodiment the second supplement packet is given as an afternoon or evening (PM) dose.

It will be understood that the supplement packets given to each patient may vary according to the results of the blood, urine and DNA screens. For example, if a particular patient contains SNPs indicating a methylation deficiency, the oral supplements may contain additional amounts of agents that promote methylation, such as MTHF.

If the screening results indicate toxic amounts of heavy metals, the supplement packets may be augmented with a chelating agents, such as calcium disodium ethylene diamine tetraacetic acid ($CaNa^2$ EDTA) or the like.

Similarly, if the test results indicate a particularly high level of free radicals or oxidized species, additional amounts of NAC can be given to stimulate production of the antioxidant glutathione by the body.

Melatonin is preferably provided in a PM oral dose to promote sleep.

After starting the patient on the oral supplement packets (about 3-4 days prior to beginning the parenteral detoxification treatment) the patient preferably continues the oral regimen during and between the detoxification treatments, for about 2 weeks. The oral vitamin and mineral supplement regimen may be discontinued following discharge from the detoxification treatment.

The composition is preferably administered parenterally at a rate such that 1000 cc are "run" into the patient in about 2 to about 4 hours. The rate can be speeded up if necessary, to control withdrawal symptoms, muscle cramping or spasm, or shakiness.

Below, non-limiting examples are given of formulas for the composition of this invention.

In another example the method of the invention comprises parenteral administration of the following compositions:

A) IV Bag 1: which comprises at least about 10 g of ascorbic acid in a substantially isotonic solution.

Preferably, IV Bag 1 also contains:
  one or more vitamin comprising: Vitamin B1 (thiamine), Vitamin B2 (riboflavin), Vitamin B3 (niacin or nicotinamide), Vitamin B9 (folate or folic acid), Vitamin B5, Vitamin B6, B7 (biotin), and/or B12;
  one or more mineral comprising: a major mineral such as soluble calcium (i.e., calcium gluconate), sodium, potassium, magnesium, phosphorus and sulfur; a trace mineral, such as iron, zinc, iodine, selenium, copper, manganese, fluorine, chromium and molybdenum.

one or more amino acid comprising taurine and/or threonine.

In one example, IV Bag 1 contains amino acids, but does not contain the 20 amino acids used in human protein synthesis. In other examples IV Bag 1 contains each of the 20 amino acids used in human protein synthesis.

Vitamin B1 (thiamine) is preferably present in a concentration of from about 50 mg to about 80 mg per 100 ml. However, up to a total of about 10 g may be administered if necessary to help control tremors. Thiamine is a coenzyme in the catabolism of carbohydrates and amino acids.

Vitamin B3 (niacin (nicotinic acid) or nicotinamide) is preferably present in an amount from about 900 mg to about 1500 mg per 100 ml. Vitamin B3 is important in the DNA repair and many metabolic processes, and deficiencies in the form of the disease pellagra, commonly seen in chronic alcoholics, can lead to dementia and death.

Vitamin B5 (pantothenic acid) is present at a preferred amount of from 400 mg to about 1200 mg. Vitamin B5 is a precursor of Coenzyme A, which is involved in fatty acid synthesis and energy production in the citric acid cycle.

Vitamin B6 (Pyridoxine or Pyridoxal-5-Phosphate) (about 100 mg) is associated with the production of neurotransmitters, and is required for amino acid, carbohydrate and lipid synthesis.

Vitamin B7 (Biotin) (about 10 mg) is a necessary co-factor for many metabolic enzymes, and a deficiency in biotin can cause higher susceptibility to diabetes and diseases of the skin intestinal tract, and nervous system.

Vitamin B9 (Folate or Folic acid) (about 10 mg) is essential for human growth and development, and encourages normal nerve and proper brain functioning; may help reduce blood levels of the amino acid homocysteine, reducing risks of heart attack.

Vitamin B12 (Cobalmin/Cyanocobalamin) (about 2 mg) affects the development and maintenance of red blood cells, nerve cells, and normal myelination (covering) of nerve cells. It also aids in the production of DNA, RNA, and neurotransmitters.

In one embodiment the IV Bag I is provided in a 500 cc volume as an isotonic parenteral solution. In order to assure the stability of the ingredients, the components of IV Bag I are mixed shortly, such as 15 minutes, prior to use.

When administration of IV Bag 1 is begun, the patient is very preferably monitored by pulse, oxygen, electrocardiogram (EKG) and blood pressure. Vital signs are taken every 20 minutes for the first 2 hours, then every hour thereafter. Urine samples are taken immediately pretreatment, and again after the first day's treatment.

Typically, after administration of e.g. 50 cc of IV Bag I, the patient is given an approximately equal volume of a large dose of ascorbic acid (or a water-soluble ascorbate salt) in solution as follows:

B) IV Push 1 (IVP #1)

65 cc of a hypertonic solution containing 25 grams ascorbic acid (or a water-soluble ascorbate salt), 8.5% by weight of sodium bicarbonate as an alkalizing agent, 1% by weight of lidocaine as a local anesthetic, 5% of calcium gluconate (to treat to treat low blood calcium, high blood potassium), and 20% by weight of magnesium chloride.

The high, hypertonic concentration of ascorbic acid administered following the prior administration of lower concentrations in the isotonic IV 1 solution, is particularly important from a therapeutic perspective.

Very preferably the IV Push 1 is administered manually by a physician or under physician's supervision so that the patient's vital signs and comfort level may be monitored and administration may be spread or slowed, as appropriate, based upon the patient's comfort and safety. Preferably the 65 ccs of the IVP 1 is administered at an average rate of 1 cc/minute or more such as 1.25 ml/minute or about 1.5 ml/minute, or so.

Ascorbic acid is known to function as a very effective antioxidant at certain, generally normal to low, concentrations, and may act as an oxidizing agent at other, generally higher/pharmaceutical concentrations. Also, ascorbic acid or ascorbate is able to act as an "exciter", enhancing adrenergic and histaminergic ligand potency through an extracellular mechanism involving binding of the enhancer to the first extracellular loop of the relevant aminergic GPCR. See e.g., Robert Root-Bernstein & Patrick E. Dillon, *A Common Molecular Motif Characterizes Extracellular Allosteric Enhancers of GPCR Aminergic Receptors and Suggests Enhancer Mechanism of Action*, CURR. MED. CHEM. 21: 3673, 3774 (2014).

in addition to ascorbic acid, several other classes of compounds have also been characterized as significantly enhancing aminergic GPCR activity. These compounds include folic acid, ethylenediaminetetraacetic acid (EDTA), opiate drugs and their antagonists, opioid peptides, corticosteroids, members of the citric acid cycle, and various flavenoids. All of these compounds have been demonstrated to produce significant (three- to ten-fold) enhancement of the potency and duration of activity of aminergic compounds while having no intrinsic activity themselves on aminergic systems. See Bernstein & Dillon at 3673.

Once the IVP 1 push dose has been given, the patient is then immediately given the remainder of IV Bag 1 at about 2.5 ml/minute.

IV Push 2 (Glutathione)

Following administration of IV Bag 1, the patient is then given about 20 cc of a solution containing about 2 g of glutathione manually in an IV syringe push over about 2-4 minutes. This will assist the liver by helping prevent damage to important cellular components caused by reactive oxygen species, such as free radicals, peroxides, lipid peroxides and heavy metals.

IV Bag 2

Following the IV glutathione Push (IV Push 2), the patient may then be given a IV drip of about 50 g ascorbic acid in about 500 cc of water with 10 cc of 5% (w) calcium gluconate and 8 cc of 20% (w) magnesium chloride over about a 2 hour period.

IV Bag #3

Following the administration of IV Bag 2, the patient is then given 500 cc of sterile saline over a 1.5 hour period. The patient will be completely detoxified, even if intoxicated when the treatment was initiated, substantially without experiencing withdrawal symptoms, hallucinations, delirium tremens, pain, or other physical symptoms of drug or alcohol withdrawal. Maintenance of a healthy diet and continued restorative treatments with vitamins and minerals to mend and nourish the body help create the metal habit required to maintain sobriety once detoxification removes the physical discomfort. When sterile saline is used it is preferably a 0.9% normal solution of sodium chloride. Sodium chloride keeps electrolyte levels of the red blood cells in balance. Its normality is selected to be compatible with blood serum, so that, if injected, the solution will not appreciably alter the osmolality of blood serum or cause hemolysis of red blood cells. The saline solution irrigates the circulatory system and guards against dehydration if diarrhea develops.

It is not necessary for the patient to be sober when the first day of parenteral treatment is given. The patient should eat a good breakfast, and should list food, drink and drugs consumed in the morning prior to the visit.

In an important embodiment, and while not wishing to be bound by theory, Applicant believes that methods which combine administration of relatively low doses of ascorbic acid, such as the doses contained in the oral supplement packets (which tend to be oxidizing), followed with higher dose, parenteral administration of ascorbic acid (which tend to be reducing/antioxidizing) in a hypertonic solution, is able to first cause the complete oxidation, and thus the "labeling", of metabolic by-products and toxins for subsequent disposal by the body. The hypertonic, antioxidizing high dose of ascorbic acid will then remove free radicals and cause the reduction of residual oxidizing agents in the body. The high concentration of the hypertonic ascorbic acid dose will, by virtue to the high osmotic pressure, cause the ascorbic acid to penetrate cell membranes and be stored within the cells themselves.

Almost invariably, treatment-naive patients suffering from alcohol, opiate, barbiturate, benzodiazepine, or amphetamine addiction who are treated using the protocol described above display no symptoms of "cold turkey"-type withdrawal, seizures, delirium tremens, vomiting, severe muscle spasms, agitation, lacrimation from the nose and eyes, uncontrollable urination, nausea, and in severe cases, convulsions, respiratory failure, and cardiac arrest.

The treatment is essentially the same for patients suffering from alcohol dependency and drug dependency. Indeed, today most alcoholic patients have a drug dependency as well. For alcoholic patients, following the initial detoxification treatment, additional agents may be added such as a lipotropic formula for reducing triglyceride levels in the bloodstream. Such a formula may comprise, for example, a lipotropic formula for reducing triglyceride levels in the bloodstream comprising about 2500 mg choline bitartrate, about 150 mg betaine hydrochloride, about 15 mg d-calcium pantothenate, and about 750 mg lecithin, in a suitable pharmacological carrier. Additionally the patient may be given a digestive and pancreatic enzyme formula, N,N dimethylglycine, and a supplement of L-glutamine.

The invention is now described with reference to specific examples, which do not limit, but rather expand the scope of the present invention.

DETAILED DESCRIPTION

This invention provides a therapeutic detoxifying composition and treatment method for reducing or eliminating symptoms of drug or alcohol withdrawal. The method and compositions rapidly detoxify the subject while blocking withdrawal symptoms, while nutritionally restoring the patient's body from a malnourished state.

Illicit or commonly abused drugs and alcohol may have a high "addiction liability" (defined as a high likelihood (e.g., greater than 20%, or greater than 30%, or greater than 40%, or greater than 50%, or greater than 60% or greater than 70%) that long-term or high dose use will lead to compulsive use) and/or a high "dependence liability" (defined as a high likelihood (e.g., greater than 20%, or greater than 30%, or greater than 40%, or greater than 50%, or greater than 60% or greater than 70%) that withdrawal symptoms will occur when the SOA use ceases). The present invention is able to treat both addiction liabilities and dependence liabilities.

In addition to alcohol, examples of substances of abuse (SOAs) which are capable of treatment by this invention include, but are not limited to, heroin, opium, methodone, cocaine, marijuana, LSD, mescaline, peyote, MDA, MDMA (ecstasy) and other psychedelics, PCP, barbiturates, tobacco, amphetamines (including methamphetamine), benzodiazepines such as Valium™, Librium™ and Klonopin™), and other prescription or non-prescription drugs or medications, or toxic chemicals. Presently, it appears that this invention is capable of detoxifying any substance from the human body within a 6-8 hour period.

While not wishing to be limited by theory, Applicant believes that the present methods and compositions work by a combination of mechanisms. Vitamin C (ascorbic acid) competes with the SOA and toxic or deleterious metabolites at the cell surface and internal receptors, such as the NMDA glutamate neuroreceptor and the µ opioid receptor. The high concentrations of Vitamin C used in the present method detaches such compounds and blocks their reattachment to the receptor(s).

Such high concentrations of ascorbic acid also permit the intracellular accumulation of ascorbic acid. Such accumulation appears to be facilitated by high affinity, high specificity binding to a protein named SVCT2, and perhaps also by the transport protein SVCT1.

At low concentrations of ascorbic acid, free radicals and reactive oxidative species (ROS) are reduced by the antioxidant activity of ascorbic acid. At high concentrations of ascorbic acid, in which ascorbic acid acts as a pro-oxidant, other reactive oxidative species may be further oxidized to increase reactivity, then neutralized by a less reactive antioxidant to neutrality.

Ascorbic acid also detoxifies inflammatory and environmental toxins, such as organic phosphates and plastics, which can cause anxiety and depression if untreated.

Finally, the methods and compositions of the present invention restore nutritional health to the individual being treated. These changes are reinforced by instruction in modifications to the patient's diet and lifestyle.

Further disclosure is provided in the example provided below, which illustrates, but does not define the invention; the invention being defined solely by the claims which conclude this specification.

Example

A female patient is 32 years old and is addicted to heroin, which she has been using for 2 years, after developing a dependence on prescription opiates.

First Patient Encounter

An extensive patient medical history is taken, and a physical examination conducted. The patient presents as thin and somewhat undernourished, but otherwise in good health. The patient states that she is under the influence of heroin, having injected the drug approximately one hour previously. DNA (e.g. 23 and me), blood and urine is taken, and lab tests ordered for SNPs, homocystiene, Brain Derived Neurotrophic Factor (BDNF), cortisol, DHEA, ACTH, ceruloplasmin, copper, zinc, iron, selenium, Vitamins B-1, B-3, B-5, B-6, B-7, B-9 & B-12, glyphosate, a screen for common drugs of abuse in blood and urine, G6PD, CMP, CBC, hepatitis panel (A, B and C)), and an HIV test.

The patient is provided with oral supplements comprising morning (AM) and evening (PM) packages, which are buffered to physiological pH. Patient will take oral supplements from this first encounter until one day following discharge; approximately 2 weeks.

The AM Package comprises:

| | |
|---|---|
| Ascorbic Acid | 1 gram |
| Super B complex vitamins | 250 mg |
| SAM-e (S-adenosylmethionine) | 400 mg |
| MTHF | 100 mg |
| NAC | 600 mg |
| Tyrosine | 500 mg |

The PM Package comprises:

| | |
|---|---|
| Ascorbic Acid | 1 gram |
| Glutamine | 500 mg |
| GABA | 500 mg |
| Tryptophan/5-hydroxytryptophan (5-HTP) | 1000 mg (Tryp)/100 mg (5-HTP) |
| Vitamin D | 5000 units |
| Melatonin | 0.5 mg |
| Selenium/Zinc | 2 µg (Se)/25 mg (Zn) |

The initial detox treatment is scheduled within 3 to 4 days after the initial patient encounter. During this time the test results are obtained and analyzed. The patient is found not to be G6PD deficient, or positive for HIV or hepatitis A, B or C. During this time between the first and second Patient Encounter (first day of treatment) the oral dose of ascorbic acid is preferably increased from 1 gram twice a day to 2 grams per day over the 3 to 4 day time interval.

Second Patient Encounter (First Day of Treatment)

The patient is provided a light breakfast of fruit and coffee, and urine is taken prior to treatment. The patient indicates that she has injected a dose of heroin earlier in the morning.

The following ingredients were mixed approximately 1 hour prior to treatment; it will be understood that minor variation in the amounts of these ingredients is permitted and falls within the scope of the invention:

| IV BAG #1 | |
|---|---|
| Ascorbic Acid | 10 grams |
| Taurine | 250 mg |
| Threonine | 100 mg |
| Zinc Sulfate | 3 mg |
| Selenium (Sodium Selenite) | 200 mcg |
| Trace minerals | 2 ml |
| Potassium chloride | 4 meq |
| Calcium gluconate | 50-75 mg |
| Vitamin B6 | 100 mg |
| Vitamin B5 | 250 mg |
| Folic Acid | 10 mg |
| Thiamine | 100 mg |
| Nicotinamide | 100 mg |
| Sterile Water for infusion | q.s. to 500 cc |

| IVP #1 (Syringe "Push" #1) | |
|---|---|
| Ascorbic Acid (50% (w) soln) | 25 grams (50 cc); final 36% (w) |
| Sodium bicarbonate (8.5% (w) soln) | 10 cc; final 1.2% (w) |
| Lidocaine (1% (w) soln) | 0.5 cc; final 0.0072% (w) |
| Calcium gluconate (5% (w) soln) | 2.5 cc; final 0.14% (w) |
| Magnesium chloride (20% (w) soln) | 2.5 cc; final 0.57% (w) |

The hypotonic aqueous solution IVP #1 is loaded into a syringe in preparation for use.

The patient is made comfortable on a reclining chair, and vital signs (e.g., heart rate, respiration rate, blood pressure, blood $O_2$, temperature) are monitored every 20 minutes for the first two hours (and during "push" procedures), then hourly during the remainder of the procedure. The patient is encouraged to relax, and is offered reading material and headphones playing soothing music as a relaxation aid. After about 20 minutes, the patient indicates she is experiencing neither any sensation of being under the influence of heroin nor any craving for heroin or discomfort, such as withdrawal symptoms, associated with the discontinuation of the use of heroin.

The contents of IV Bag #1 (an isotonic solution) are started intravenously, at a rate of about 2.5 ml/minute. After 15-20 minutes (i.e., after about 50 cc of IV Bag #1 have been administered), the infusion of IV Bag #1 is stopped, and IVP #1 is administered manually using the syringe at an average rate of about 2.3 ml/min. This rate can be speeded or slowed, as necessary, depending on the patient's comfort level. The IVP #1 solution is quite dense, and the patient may experience some minor pain or discomfort during the "push" procedure administration. Vital signs are monitored while the IVP #1 solution is injected manually. The lidocaine added to IVP #1 renders the degree of discomfort reported by the patient during this process minimal.

Following administration of IVP #1 (about 30 minutes), the patient is administered the remainder of IP Bag 1 at an infusion rate of about 2.5 ml/min. Following administration of IVP #1 the patient shows no signs of heroin intoxication, and no withdrawal symptoms. The patient reports no withdrawal symptoms or related discomfort and no craving for heroin.

During administration of IV Bag 1, a fresh aqueous solution labeled IVP #2 is made, consisting of 20 cc of 10% (w) glutathione. Additionally, IV Bag #2 is also made up in advance, comprising 500 cc of an aqueous sterile solution containing 50 g ascorbic acid, 10 cc of 5% (w) calcium gluconate, and 5 cc of 20% (w) magnesium chloride.

Following administration of the remainder of IV Bag #1, the 20 cc IVP #2 solution is loaded into a syringe and manually administered within a time period of 2-10 minutes; preferably within about 2 to about 6 minutes, or within about 2 to about 4 minutes. As with IVP #1, the patient is monitored during the IVP #2 administration, and the rate of administration is slowed if the patient experiences any discomfort. Glutathione is a major and highly conserved antioxidant in plants, animals, fungi, bacterial and some archaea, and is capable of preventing damage to important cellular components caused by reactive oxygen species such as free radicals, peroxides, lipid peroxides, and heavy metals.

Following administration of IVP #2, IV Bag #2 is administered over a 2-hour period of time (i.e., at an average rate of about 4 ml/min. This 500 cc IV Bag #2 contains 10% (w) ascorbic acid, as well as calcium and magnesium for cardiac and nervous system health.

Finally, IV Bag #3 (sterile isotonic saline solution) is administered at about the same rate (about 500 cc over a 2 hour period) to clear out the neutralized reactive oxidative species and metabolic by-products.

Following the procedure, a urine sample is taken before the patient leaves the facility, and the patient is then sent home with orders to drink plenty of fluids, to rest and to refrain from drinking or using drugs. The patient at this point should be placed in a sober living environment, and receive psychological counseling and/or attend 12 step meetings to reinforce the physical detoxification, which is well underway at the end of the first detoxification treatment.

Third Patient Encounter (Day after Initial Detox)

Urine is collected before the IV treatment. IV treatment is simply 500 cc to 1000 cc of sterile saline, administered at a rate of about 250 cc per hour. Urine is again collected after the IV treatment. The urine samples are collected to monitor substances of abuse and their metabolites. The urine samples will reveal not only the presence or absence or reported drugs (including alcohol) but any unreported drugs, such as nicotine.

Fourth Patient Encounter (Third Day Following Initial Detox)

Urine is collected before the IV treatment. IV treatment is identical to that of the Second Patient Encounter, except that IV Push #1 is not administered. Thus, IV Bag 1 is administered, followed by IVP #2, and then IV Bag 2 and IV Bag 3. The administration and flow ratesz of the IV Bags and IV push #2 are the same as in the Second Patient Encounter. Urine is again collected after the IV treatment.

Following the Fourth Patient Encounter on days 4-9, the patient is not seen, but is referred to a sober living environment, with healthy, "paleo" diet-type meals (i.e., no processed foods, no starches or processed meats, fresh vegetables, fruits, whole nuts and grains.

Fifth Patient Encounter (Tenth Day Following Initial Detox)

Urine is collected before the IV treatment. IV treatment is identical to that of the Second Patient Encounter, except that IV Push #1 is not administered. Thus, IV Bag 1 is administered, followed by IVP #2, and then IV Bag 2 and IV Bag 3. The administration and flow rates of the IV Bags and IV Push #2 are the same as in the Second Patient Encounter. Urine is again collected after the IV treatment.

Blood samples are then taken for labs showing: hormone levels (e.g., ACTH (Adrenocorticotropic hormone), cortisol, testosterone, dihydrotestosterone, DHEA, estrogens, thyroid hormones), homocystiene levels, CBC, CMP, GGT (gamma-glutamyltransferase) test of liver function), lactic acid dehydrogenase (LDH) test of cellular damage and kidney and liver disease, triiodothyronine (T3) test (thyroid function), Reverse T3 test (to eliminate a diagnosis of hyperthyroidism), thyroid-stimulating hormone (TSH) test, lipase/amylase tests of pancreatic function. WHAT FURTHER ACTIONS (IF ANY) ARE TAKEN BASED ON THE RESULTS OF THESE TESTS? Ref #8

Assuming these tests confirm the restoration of the patient's basic nutritional health, the patient has now completed the detoxification regimen, without withdrawal symptoms and without craving for heroin. The patient continues to obtain psychological counseling and to attend 12 step meetings to reinforce her transition from a drug-using life to a drug-free life.

Other aspects and embodiments of the invention will be apparent from the claims that follow this specification. To the extent that a plurality of inventions may be disclosed herein, any such invention shall be understood to have been disclosed herein alone, in combination with other features or inventions disclosed herein, or lacking any feature or features not explicitly disclosed as essential for that invention. For example, the inventions described in this specification can be practiced within elements of, or in combination with, any other features, elements, methods or structures described herein. Additionally, features illustrated herein as being present in a particular example are intended, in other examples of the present invention, to be explicitly lacking from the invention, or combinable with features described elsewhere in this patent application, in a manner not otherwise illustrated in this patent application or present in that particular example. The scope of the invention shall be determined solely by the language of the claims.

Thus it will be understood that the various descriptions of the invention provided herein illustrate presently preferred examples of the invention, but that the invention is not limited to the examples provided, or to the specific configurations and relation of elements unless the claims specifically indicate otherwise. Based upon the present disclosure a person of ordinary skill in the art will immediately conceive of other alternatives to the specific examples given, such that the present disclosure will be understood to provide a full written description of each of such alternatives as if each had been specifically described.

What is claimed is:

1. A method for attenuating symptoms of withdrawal to drugs or alcohol in a patient, comprising parenterally administering to said patient a solution, said solution comprising a prooxidative dose of at least about 10 g of ascorbic acid at a concentration of greater than 0.2 grams/ml and an effective amount of a local anesthetic, at an average rate of at least about 0.5 ml/minute.

2. The method of claim 1 comprising parenterally administering to said patient at least 25 g of ascorbic acid in solution.

3. The method of claim 1 wherein said solution has an ascorbic acid concentration of about 0.5 g/ml.

4. The method of claim 1 wherein said solution is parentarally administered at an average rate of about 2 ml/min.

5. The method of claim 1 wherein said local anesthetic is present at is present at a final concentration corresponding to an analgesic activity equivalent to that of an otherwise identical solution containing from about 0.01% (w) to about 0.005% (w) of lidocaine.

6. The method of claim 1, comprising parenterally administering to said patient:
   a) a dose of about 50 ml of an antioxidant solution comprising about 2% (w/v) ascorbic acid at a rate of about 2.5 ml/min; and
   b) a dose of a hypertonic solution comprising an prooxidative dose of ascorbic acid at a rate of greater than about 0.5 ml/minute.

7. The method of claim 6 wherein the local anesthetic is present at a final concentration corresponding to an analgesic activity equivalent to that of an otherwise identical solution containing from about 0.01% (w) to about 0.005% (w) of lidocaine.

8. The method of claim 7 further comprising the step:
   c) parenterally administering a solution comprising about 2 g glutathione at a concentration of about 0.1 g/ml.

9. The method of claim 1 in which administration of diarrhea-inducing amounts of oral ascorbic acid is avoided.

10. A composition comprising a hypertonic solution comprising at least about 20 g of ascorbic acid at a concentration of at least about 30% by weight and an amount of a local anesthetic is present at a final concentration corresponding to an analgesic activity equivalent to that of an otherwise identical solution containing from about 0.01% (w) to about 0.005% (w) of lidocaine.

11. The composition of claim 10 wherein the local anesthetic is lidocaine.

12. A method for attenuating the deleterious effects of reactive oxygen species, comprising administering parenterally administering to a subject in need thereof a hypertonic solution comprising at least 10 g of ascorbic acid at a concentration of at least about 0.2 grams/ml and an amount of a local anesthetic is present at a final concentration corresponding to an analgesic activity equivalent to that of an otherwise identical solution containing from about 0.01% (w) to about 0.005% (w) of lidocaine.

13. The method of claim 12 wherein the patient is parenterally administered about 30 to about 70 cc of a first solution containing about 2% (w) ascorbic acid in a volume of from about 50 cc to about 75 cc over about 30 minutes immediately before the hypertonic solution is parenterally administered.

14. The method of claim 13 wherein about 500 cc of a second solution containing about 2% (w) ascorbic acid is parenterally administered over about 2 hours immediately after the hypertonic solution is parenterally administered.

15. The method of claim 14 wherein, following administration of the second solution, a third solution containing about 2 g of glutathione is parenterally administered manually over about 2-5 minutes.

16. The method of claim 15 comprising parenterally administering a fourth solution containing about 2% (w) ascorbic acid in a volume of from 250 cc to about 1000 cc.

17. The method of claim 14 wherein at least one of said solutions contains Vitamin B5, Vitamin B6, thiamine, and amino acids.

* * * * *